(12) United States Patent
List (10) Patent No.: US 11,406,759 B2
(45) Date of Patent: Aug. 9, 2022

(54) METHOD AND DEVICES FOR PRESSURE DETERMINATION IN AN INSULIN PUMP

(71) Applicant: Roche Diabetes Care, Inc., Indianapolis, IN (US)

(72) Inventor: Hans List, Mannheim (DE)

(73) Assignee: Roche Diabetes Care, Inc., Indianapolis, IN (US)

(*) Notice: Subject to any disclaimer, the term of this patent is extended or adjusted under 35 U.S.C. 154(b) by 787 days.

(21) Appl. No.: 16/362,891

(22) Filed: Mar. 25, 2019

(65) Prior Publication Data
US 2019/0298916 A1    Oct. 3, 2019

(30) Foreign Application Priority Data
Mar. 27, 2018   (EP) .................................... 18164202

(51) Int. Cl.
*A61M 5/168* (2006.01)
*G01L 9/00* (2006.01)
(Continued)

(52) U.S. Cl.
CPC ........ *A61M 5/16831* (2013.01); *A61M 5/142* (2013.01); *G01L 1/20* (2013.01);
(Continued)

(58) Field of Classification Search
CPC .............. A61M 5/16831; A61M 5/142; A61M 2005/16863; A61M 2205/0216;
(Continued)

(56) References Cited

U.S. PATENT DOCUMENTS

| 5,184,107 A | 2/1993 | Maurer |
| 5,872,320 A | 2/1999 | Kamentser et al. |

(Continued)

FOREIGN PATENT DOCUMENTS

| CN | 107735798 A | 2/2018 |
| WO | WO 02/38204 A2 | 5/2002 |

OTHER PUBLICATIONS

English translation of the extended European search report, EP 18 164 202.6, dated Nov. 12, 2018, 5 pages.

*Primary Examiner* — Marrit Eyassu
(74) *Attorney, Agent, or Firm* — Bose McKinney & Evans LLP (57) ABSTRACT

A method for connecting a force sensor to a circuit board is disclosed. A circuit board having first and second conductive leads located on the same surface of the circuit board is provided. Also provided is a force sensor with a first flexible contact tab having a first contact pad and a second flexible contact tab having a second contact pad. The first contact pad is arranged to face the first conductive lead. A first conductive rubber element establishes an electrical connection between the first contact pad and the first conductive lead, and the second contact pad and the second conductive lead are arranged to face in the same direction. A second conductive rubber element establishes an electrical connection between the second contact pad and the second conductive lead. Also disclosed are an associated device for determining fluid pressure in an insulin pump and an insulin pump.

18 Claims, 4 Drawing Sheets

(51) Int. Cl.
*H05K 1/11* (2006.01)
*A61M 5/142* (2006.01)
*H05K 1/02* (2006.01)
*H05K 1/18* (2006.01)
*G01L 5/00* (2006.01)
*G01L 1/20* (2006.01)

(52) U.S. Cl.
CPC .......... *G01L 5/0038* (2013.01); *G01L 9/0051* (2013.01); *H05K 1/028* (2013.01); *H05K 1/11* (2013.01); *H05K 1/181* (2013.01); *A61M 2005/16863* (2013.01); *A61M 2205/0216* (2013.01); *A61M 2205/0233* (2013.01); *A61M 2205/332* (2013.01); *A61M 2205/3327* (2013.01); *A61M 2205/3344* (2013.01); *A61M 2207/00* (2013.01); *H05K 2201/10151* (2013.01)

(58) Field of Classification Search
CPC .... A61M 2205/0233; A61M 2205/332; A61M 2205/3327; A61M 2205/3344; A61M 2207/00; G01L 1/20; G01L 5/0038; G01L 9/0051; H05K 1/028; H05K 1/11; H05K 1/181; H05K 2201/10151
USPC .......................................................... 73/715
See application file for complete search history.

(56) References Cited

U.S. PATENT DOCUMENTS

| 6,423,029 | B1 | 7/2002 | Elsberry | |
|---|---|---|---|---|
| 2010/0100052 | A1* | 4/2010 | Eckhardt | A61M 5/14 604/93.01 |
| 2011/0160655 | A1* | 6/2011 | Hanson | A61M 5/14248 604/533 |
| 2012/0096953 | A1* | 4/2012 | Bente, IV | G01L 1/2231 73/862.53 |
| 2016/0339431 | A1* | 11/2016 | Shmilovich | B01L 3/502715 |
| 2018/0322323 | A1 | 11/2018 | Ran et al. | |

* cited by examiner

METHOD AND DEVICES FOR PRESSURE DETERMINATION IN AN INSULIN PUMP

RELATED APPLICATIONS

This application claims priority to EP 18 164 202.6, filed Mar. 27, 2018, the entire disclosure of which is hereby incorporated herein by reference.

BACKGROUND

This disclosure relates to a method for connecting a force sensor to a circuit board of an insulin pump, to a device for determining a pressure of a fluid in an insulin pump and to an insulin pump comprising the device. The method and devices according to this disclosure may mainly be used for delivering insulin to a user. This disclosure may both be applied in the field of home care as well as in the field of professional care, such as in hospitals. Other applications are generally feasible.

Delivering medicine to a user, specifically insulin delivery, plays an important role in the prevention and treatment of diseases, in particular, in the treatment of diabetes mellitus. In addition to using injection pens or syringes, insulin delivery may specifically be performed by using insulin pumps.

Despite the advantages of state of the art pumps for delivering insulin, several technical challenges remain. Thus, occurring occlusions generally lead to limitation of the amount of delivered insulin or even to failure to deliver insulin at all. In the field of delivering medicine, specifically in the field of insulin delivery, control of the exact amount of medicine, specifically insulin, delivered to the user, in particular delivered into the human or animal body, is critical and needs to be monitored closely. Consequently, detecting occurring occlusions, preferably immediate detection of occurring occlusions, is desirable. Thus, occlusion sensors for detecting occurring occlusions need to be contacted at a high precision and reliability. On the other hand, a user is generally required to wear the insulin pump on his or her body at all times, thus leading to a preferably small and compact construction of the insulin pump and its components.

SUMMARY

This disclosure addresses the above-mentioned technical challenge. Specifically, a method, a device and an insulin pump providing a high degree of precision and reliability in electrically contacting a sensor, while, still, allowing for a small and compact construction is taught by this disclosure.

As used in the following, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B," "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one," "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once.

Further, it should be understood that all terms used throughout this disclosure and claims, regardless of whether said terms are preceded by the phrases "one or more, "at least one, or the like, should not receive a singular interpretation unless it is made explicit herein. That is, all terms used in this disclosure and claims should generally be interpreted to mean "one or more" or "at least one."

Further, as used in the following, the terms "preferably," "more preferably," "particularly," "more particularly," "specifically," "more specifically" or similar terms are used in conjunction with optional features, without restricting alternative possibilities. Thus, features introduced by these terms are optional features and are not intended to restrict the scope of the claims in any way. This disclosure may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect of this disclosure, a method for connecting a force sensor to a circuit board of an insulin pump is disclosed. The method comprises the steps disclosed in the following. The steps specifically may be performed in the given order. Still, a different order is possible. The method may comprise additional steps which are not mentioned. It is further possible to perform one or more of the method steps repeatedly. Further, two or more of the method steps may be performed in a timely overlapping fashion or simultaneously.

The method comprises the following steps:
a) providing the circuit board, preferably a flexible circuit board, comprising at least one first conductive lead and at least one second conductive lead, wherein the first conductive lead and the second conductive lead are located on the same surface of the circuit board;
b) providing the force sensor having at least one flexible first contact tab and at least one flexible second contact tab, wherein each contact tab comprises a contact pad, wherein the contact pad of the first contact tab and the contact pad of the second contact tab are arranged on opposite sides relative to each other;
c) arranging the first contact tab such that the contact pad of the first contact tab faces the first conductive lead of the circuit board;
d) arranging a first conductive rubber element such that an electrical connection between the contact pad of the first contact tab and the first conductive lead is established;
e) arranging the second contact tab such that the contact pad of the second contact tab and the second conductive lead face in the same direction; and
f) arranging a second conductive rubber element such that an electrical connection between the contact pad of the second contact tab and the second conductive lead is established.

The term "circuit board" as used herein is a broad term and is to be given its ordinary and customary meaning to a person of ordinary skill in the art and is not to be limited to a special or customized meaning. The term specifically may refer, without limitation, to a device which mechanically supports and electrically connects two or more electronic components or electrical components using conductive leads, traces, tracks, pads and other conductive features. The circuit board specifically may be or may comprise a printed circuit board. The circuit board may comprise a substrate or carrier, such as a board-shaped or plate-shaped substrate or a substrate foil, and one or more conductive layers disposed thereon on one or more than one side, such as one or more metallic layers, wherein conductive elements such as one or more conductive leads, traces, tracks, pads and other conductive features are formed out of the one or more conductive layers. The substrate specifically may be made of a plastic material. One or more electronic components may be attached to the circuit board, such as by soldering or conductive glue, to both electrically connect and mechanically fasten the components to the circuit board. Additionally or alternatively, the circuit board may for example be or may comprise a Molded Interconnect Device (MID), such as for example a three-dimensional circuit carrier comprising three dimensional conductive leads or tracks.

The circuit board specifically may be at least partially flexible, i.e., may fully or partially be designed as a flexible circuit board. Thus, the substrate of the circuit board, specifically the printed circuit board, may fully or partially be made of a flexible material, such as a flexible foil, e.g., polyimide. Thus, the circuit board may fully or partially be designed as a flex circuit board.

The circuit board comprises at least one first conductive lead and at least one second conductive lead, wherein the first conductive lead and the second conductive lead are located on the same surface of the circuit board. The term "conductive lead" as used herein is a broad term and is to be given its ordinary and customary meaning to a person of ordinary skill in the art and is not to be limited to a special or customized meaning. The term specifically may refer, without limitation, to an electrically conductive element such as a trace, track or lead disposed at a surface of the circuit board which is configured for electrically connecting two or more points or regions on the surface of the circuit board. The trace may fully or partially be covered by an insulating material such as a resin. The conductive lead, additionally or alternatively, further may also comprise one or more electrical contact pads or other accessible electrical structures disposed at a surface of the substrate and having at least one electrically conductive surface which is accessible, e.g., for being contacted by one or more electrical components.

The terms "first" and "second" as used herein are used as nomenclatures, only. No ranking or order is inherent in these terms.

The first and second conductive leads are located on one and the same surface of the circuit board, e.g., on one and the same side. Thus, the substrate of the circuit board may have a flat shape, with a first surface and a second surface, wherein the first and second surfaces are located on opposing sides of the substrate and, as an example, are essentially parallel to each other. The first and second conductive leads may be located on the same surface, e.g., both on the first surface or both on the second surface. The other surface, in each case, may remain free of conductive leads or structures, or, alternatively, may carry one or more additional electrical structures, which, however, are not required for the method as disclosed herein.

The term "force sensor" as used herein is a broad term and is to be given its ordinary and customary meaning to a person of ordinary skill in the art and is not to be limited to a special or customized meaning. The term specifically may refer, without limitation, to an arbitrary device which is capable of generating at least one sensor signal, such as at least one electrical sensor signal, e.g., an analogue or digital sensor signal, correlating with a force or pressure exerted onto at least one pressure-sensitive surface or pressure-sensitive element of the force sensor. Various types of force sensors are generally known to the skilled person. As an example, the force sensor may comprise at least one deformable surface, such as a membrane, with one or more electrical resistors disposed thereon, wherein the exertion of a force or pressure deforms the deformable surface and the at least one electrical resistor and, thereby, changes the Ohmic value or resistivity of the electrical resistor, which may be used as a signal or for generating a signal indicative of the force or pressure.

The force sensor has at least one flexible first contact tab and at least one flexible second contact tab, wherein the terms "first" and "second," again, are used for the purpose of nomenclature, only. More than two tabs may be present. The term "flexible contact tab" as used herein is a broad term and is to be given its ordinary and customary meaning to a person of ordinary skill in the art and is not to be limited to a special or customized meaning. The term specifically may refer, without limitation, to a part of the force sensor which is flexible, which protrudes from the force sensor and which contains at least one electrical element for electrically contacting the force sensor. As an example, the force sensor may comprise a substrate such as a flexible substrate, e.g., a flexible circuit board, wherein the first and second contact tabs are end portions of the flexible substrate, e.g., the flexible circuit board. As an example, the first and second contact tabs each may be strip-shaped, e.g., forming parallel strips, with one end of each strip being connected to the substrate and one free end, each.

Each contact tab comprises a contact pad. The term "contact pad" as used herein is a broad term and is to be given its ordinary and customary meaning to a person of ordinary skill in the art and is not to be limited to a special or customized meaning. The term specifically may refer, without limitation, to an element such as a pad, being fully or partially made of at least one electrically conductive material, having an open or accessible electrically conductive surface configured for being electrically contacted. The contact pad may have an arbitrary shape, such as a rectangular shape, a round shape, an oval shape a polygonal shape or the like. The contact pad may be electrically connected to at least one electrically conductive lead which, as an example, electrically connects the contact pad with the actual force sensor, such as with the at least one resistor discussed above.

The contact pad of the first contact tab and the contact pad of the second contact tab are arranged on opposite sides relative to each other. Thus, as an example, the force sensor may have a substrate having a first side, e.g., a first side facing in a first direction, and a second side, e.g., a second side facing in a second direction opposite the first direction, with the first side and the second side, e.g., being parallel to each other. Thus, the substrate may be a flat substrate with two parallel, opposing surfaces. The contact pad of the first contact tab may be located on the first side, and the contact pad of the second contact tab may be located on the second side, or vice versa.

Thus, the first conductive lead and the second conductive lead of the circuit board are located on the same surface of the circuit board, whereas the contact pad of the first contact tab and the contact pad of the second contact tab of the force sensor are arranged on opposite sides relative to each other. The circuit board may be a one-sided circuit board, whereas the force sensor is two-sided and comprises contact pads on both sides.

Now the first contact tab and the second contact tab of the force sensor are electrically connected to the circuit board in different ways.

The first contact tab of the force sensor is connected to the circuit board in a face-to-face fashion. For this purpose, the first contact tab is arranged such that the contact pad of the first contact tab faces the first conductive lead of the circuit board. For electrically connecting the contact pad of the first contact tab and the first conductive lead of the circuit board, at least one first conductive rubber element is used. For this purpose, the first conductive rubber element is arranged such that an electrical connection between the contact pad of the first contact tab and the first conductive lead is established.

Contrarily, the second contact tab of the force sensor is connected to the circuit board in a back-to-face fashion. For this purpose, the second contact tab of the force sensor is arranged such that the contact pad of the second contact tab and the second conductive lead face in the same direction. For electrically connecting the contact pad of the second contact tab and the second conductive lead, a second conductive rubber element is used. For this purpose, the second conductive rubber element is arranged such that an electrical connection between the contact pad of the second contact tab and the second conductive lead is established. Various possibilities exist for arranging the second conductive rubber element. As an example, the second contact tab and the second conductive lead may be arranged next to each other, and the second conductive rubber element may be pressed on both elements, such that a part of the second conductive rubber element at least partially covers the contact pad of the second contact tab and another part of the second conductive rubber element at least partially covers the second conductive lead. Specifically, the second electrically conductive element may allow electrically connecting the contact pad of the second contact tab and the second conductive lead even in case a height difference or gap exists between the two surfaces. Specifically, a height difference or gap may exist between the contact pad of the second contact tab and the second conductive lead and the height difference may be compensated via the second conductive rubber element. In particular, the second conductive rubber element may be pressed on both the second contact tab and the second conductive lead, thereby compensating the height difference or gap between the contact pad of the second contact tab and the second conductive lead.

The term "conductive rubber element" as used herein is a broad term and is to be given its ordinary and customary meaning to a person of ordinary skill in the art and is not to be limited to a special or customized meaning. The term specifically may refer, without limitation, to an elastomeric element having electrically conductive properties. The term further specifically may refer, without limitation, to an arbitrary material or a composition of materials adapted to allow a flow of an electrical current in one or more directions and further adapted to be elastically deformable. In particular, the conductive rubber element may be or may comprise a material which is incompressible. Thus, as an example, the total volume of the electrically conductive elastomeric element may be unchanged in case the electrically conductive elastomeric is deformed or compressed. The conductive rubber element specifically may comprise at least one electrically conductive rubber, specifically at least one rubber material filled with electrically conductive particles, more specifically filled with one or more of carbon particles or metal particles. Specifically, the electrically conductive rubber may contain a silicone rubber. In particular, the electrically conductive rubber element for example may be or may comprise a foam element, such as a conductive rubber foam. Specifically, the conductive rubber foam may be compressible. As an example, the compressible conductive rubber foam may lead to a compressibility of the conductive rubber element, e.g., to the body of the conductive material. In particular, the use of the conductive rubber foam may be advantageous in cases where high contact forces are difficult to support. Other options exist.

As an example, the conductive rubber element may be or may comprise at least one electrically conductive rubber, as will be outlined in further detail below. As an example, the conductive rubber element may comprise at least one elastomeric matrix material, with one or more filling materials disposed therein, such as dispersed therein, e.g., one or more of at least one metal powder and/or at least one conductive carbon powder. Additionally or alternatively, the conductive rubber element may be or may comprise at least one elastomeric matrix material with one or more electrically conductive fibers, beads or leads disposed therein, such as one or more of fibers, beads or leads made of one or more of metal or conductive carbon. However, different types of electrically conductive rubber may exist. Specifically, the electrically conductive rubber may comprise a non-conductive matrix, such as, for example, silicone and/or rubber, and embedded therein, the electrically conductive rubber may comprise conductive particles, such as, for example, particles comprising one or more of metal or conductive carbon. A grade, ratio or degree of filling may refer to a quantity of particles embedded within the non-conductive matrix. Specifically, the grade of filling with the conductive particles may be such, that the conductive particles electrically contact one another, such as to provide conductive paths through the non-conductive matrix, e.g., through a bulk material. A specific resistance of the electrically conductive rubber comprising the conductive particles embedded within the non-conductive matrix may be, for example, less than 1 Ohm cm. Thus, specifically, the specific resistance of said electrically conductive rubber, e.g., a first type of the electrically conductive rubber, may be quite low. However, other types of the electrically conductive rubber may have a much higher specific resistance, such as for example 100 Ohm cm, or higher. The electrically conductive rubber having such a high specific resistance, e.g., a second type of the electrically conductive rubber, may comprise a conductive matrix, specifically a matrix of inherently conductive rubber, such as, for example, silicon rubber having molecular dispersed carbon. Combinations of different types of electrically conductive rubber however, may also be conceivable. For example, a combination of the first and second type of the electrically conductive rubber, e.g., a third type of the electrically conductive rubber, may comprise conductive particles, specifically metal particles, embedded within the inherently conductive rubber matrix.

Steps c) and d) specifically may be performed in such a way that the first conductive rubber element is sandwiched in between the first contact tab and the circuit board.

Therein, a first side of the first conductive rubber element electrically may contact the contact pad of the first contact tab and a second, opposing side of the first conductive rubber element electrically may contact the first conductive lead.

As outlined above, steps e) and f) specifically may be performed such that the second conductive rubber element partially overlaps with the second contact tab and partially overlaps with the second conductive lead. Thus, as discussed above, the second contact tab and the second conductive lead may at least partially be located next to each other, e.g., by placing the second contact tab on a surface of the circuit board next to the second conductive lead. The second conductive rubber element may be located on top of both, thereby electrically interconnecting these elements, by at least partially covering both the contact pad of the second contact tab and the second conductive lead. Therein, a first side of the second conductive rubber element may electrically contact the contact pad of the second contact tab and the first side of the second conductive rubber element further electrically may contact the second conductive lead.

Specifically, as outlined above, the second conductive rubber element may compensate a height difference between the contact pad of the second contact tab and the second conductive lead. In particular, the height difference between the two surfaces may be compensated by the second conductive rubber element being located on top of both surfaces, specifically on top of the contact pad of the second contact tab and the second conductive lead. Particularly, the height compensation may be possible due to the elastomeric matrix material comprised by the conductive rubber element allowing the conductive rubber element to adapt its form to the elements to be electrically connected. Specifically, the second conductive rubber element may be able to adapt its form to the contact pad of the second contact tab and to the second conductive lead, thereby compensating the possible height difference.

As outlined above, the second contact tab specifically may be in physical contact or in touch with the circuit board. Thus, specifically, a backside of the second contact tab may be in physical contact or in touch with the circuit board. Therein, the term "backside" specifically may refer to a side of the second contact tab opposing the side on which the contact pad of the second contact tab is arranged. The backside of the second contact tab thus, specifically, may be arranged on a side or maybe the side opposite of the contact pad comprised by the second contact tab.

In a further aspect, a device for determining a pressure of a fluid in an insulin pump is disclosed. The fluid specifically may be insulin. The device specifically may be a device for occlusion detection in the insulin pump, i.e., a device which detects unwanted blockages within the fluid path of the insulin pump, including the pump itself as well as to being directly or indirectly connected to the insulin pump. The term "insulin pump" as used herein is a broad term and is to be given its ordinary and customary meaning to a person of ordinary skill in the art and is not to be limited to a special or customized meaning. The term specifically may refer, without limitation, to a device for administering insulin by using at least one pump.

The device comprises:
  a circuit board, preferably a flexible circuit board, comprising at least one first conductive lead and at least one second conductive lead, wherein the first conductive lead and the second conductive lead are located on the same surface of the circuit board;
  a force sensor having at least one flexible first contact tab and at least one flexible second contact tab, wherein each contact tab comprises a contact pad, wherein the contact pad of the first contact tab and the contact pad of the second contact tab are arranged on opposite sides relative to each other; and
  at least two conductive rubber elements;
  wherein the first contact tab is arranged such that the contact pad of the first contact tab faces the first conductive lead of the circuit board, wherein a first conductive rubber element is arranged such that electrical connection between the first contact tab and the first conductive lead is established, wherein the second contact tab is arranged such that the contact pad of the second contact tab and the second conductive lead face in the same direction, wherein a second conductive rubber element is arranged such that an electrical connection between the contact pad of the second contact tab and the second conductive lead is established.

For possible definitions and options, reference may be made to the description of the method given above. The device specifically may be produced by using the method described above.

The device further may comprise a housing. As used herein, the term "housing" is a broad term and is to be given its ordinary and customary meaning to a person of ordinary skill in the art and is not to be limited to a special or customized meaning. The term specifically may refer, without limitation, to a basically arbitrary element which is configured for fully or partially enclosing one or more components and for providing protection for these one or more components, such as against mechanical influence and/or humidity. The housing, specifically, may be or may comprise a rigid housing, such as a rigid housing made of one or more of a plastic material, a metallic material or a cardboard material. The circuit board specifically may fully or partially be arranged in the housing. Additionally or alternatively, the force sensor may fully or partially be arranged in the housing. The housing specifically may comprise at least two cavities, wherein the first cavity is configured for receiving the first conductive rubber element, wherein the second cavity is configured for receiving the second conductive rubber element.

The first conductive rubber element specifically may be sandwiched in between the first contact tab and the circuit board. A first side of the first conductive rubber element electrically may contact the contact pad of the first contact tab. A second, opposing side of the first conductive rubber element electrically may contact the first conductive lead.

The second conductive rubber element partially may overlap with the second contact tab and with the second conductive lead. A first side of the second conductive rubber element electrically may contact the contact pad of the second contact tab. The first side of the second conductive rubber element further electrically may also contact the second conductive lead. Further, the second conductive rubber element may be configured for compensating a height difference between the contact pad of the second contact tab and the second conductive lead. Specifically, the elastomeric matrix material comprised by the conductive rubber element may allow for the height compensation. Specifically, the elastomeric matrix material may allow the conductive rubber element to adapt its form to the elements to be electrically connected, thereby compensating a height difference between the contact pad of the second contact tab and the second conductive lead.

A backside of the second contact tab specifically may be in physical contact with the circuit board. The backside of the second contact tab specifically may be arranged on a side opposite of the contact pad comprised by the second contact tab.

In a further aspect, an insulin pump is disclosed. The insulin pump comprises:
- at least one insulin reservoir;
- at least one pump module for delivering insulin to a user; and
- at least one device for determining a pressure of a fluid in an insulin pump as disclosed herein, such as according to any one of the embodiments described above or described in more detail below, wherein the device is arranged for determining an insulin pressure within the insulin pump.

The term "insulin reservoir" as used herein is a broad term and is to be given its ordinary and customary meaning to a person of ordinary skill in the art and is not to be limited to a special or customized meaning. The term specifically may refer, without limitation, to a hollow element or container which may fully or partially be filled with insulin. Specifically, the insulin reservoir may comprise at least one cartridge or vial which, specifically, may removably be placed within the insulin pump, such as within a housing of the insulin pump.

The term "pump module" as used herein is a broad term and is to be given its ordinary and customary meaning to a person of ordinary skill in the art and is not to be limited to a special or customized meaning. The term specifically may refer, without limitation, to a device configured for transporting or pumping a liquid, such as an electric pump for pumping a liquid such as insulin.

For possible embodiments of the device for determining the pressure of the fluid in the insulin pump, specifically for determining the pressure of the insulin, more specifically for determining our detecting occlusions within the insulin pump, reference may be made to the above-mentioned description of possible embodiments or to the embodiments disclosed in further detail below. The device specifically may determine the pressure of the fluid, specifically the insulin, within any part of the insulin pump configured for carrying or conducting the fluid, such as within the pump module itself and/or within tubing connected to the pump module, such as tubing connecting the pump module to an infusion kit for administering the fluid to a user.

The insulin pump may further comprise a controller. As an example, the controller may be configured for registering signals provided by the device for determining the pressure of the fluid in the insulin pump. As an example, the controller may be connected to at least one user interface, such as for bringing an alarm to the user's attention in case an occlusion is being detected. Thus, generally, the insulin pump may further comprise a controller operatively connected to the device for determining the pressure of the fluid in the insulin pump, the controller further being configured for detecting an occlusion in the insulin pump by using at least one signal provided by the device for determining the pressure of the fluid in the insulin pump. The controller, as an example, may comprise at least one processor and/or at least one microcontroller or ASIC. The controller may be programmed by program code for evaluating the at least one signal provided by the device for determining the pressure of the fluid in the insulin pump.

The proposed methods and devices provide a large number of advantages over known methods and devices of similar kind.

Specifically, a method may be provided for reliably connecting a force sensor or occlusion sensor to a circuit board of an insulin pump. Therein, as an example, the use of a commercially available and off-the-shelf force sensor is possible. The insulin pump, as an example, may be a small patch-pump which, as an example, may be attached to the skin of the user. Embodiments in accordance with this disclosure generally allow for very small volumes of the insulin pump. The force sensor may comprise conductive plastic sheets for connection, having their conductive surface on opposite sides, which, according to this disclosure, may be connected to the circuit board, such as the printed circuit board (PCB). The use of the conductive rubber allows for a reliable electrical connection.

The use of the conductive rubber elements provides further advantages. Thus, as outlined above, the contact pad of the second contact tab and the second conductive lead face in the same direction and are contacted by the at least one second conductive rubber element. In this case, the second conductive rubber element may extend over different levels, since the second contact tab and the contact pad located thereon is typically on a different height as compared to the second conductive lead on the printed circuit board. The second conductive rubber element thereby levels the differences in height. The use of conductive rubber elements further avoids the use of soldering, since, typically, many flexible substrates and flexible conductive leads do not withstand the heat of soldering. Further, the use of conductive adhesives may be avoided, which avoids the use of costly manufacturing lines typically involved in dispensing conductive adhesives. The electrical interconnection between the contact pad of the first contact tab faces the first conductive lead of the circuit board as well as the electrical interconnection between the contact pad of the second contact tab and the second conductive lead may take place without using material engagement such as soldering or gluing, e.g., by a pure clamping or force fit or form fit connections, e.g., by pressing the respective conductive rubber elements onto the elements to be connected electrically and/or by pressing these elements onto the respective conductive rubber elements.

Summarizing and without excluding further possible embodiments, the following embodiments may be envisaged:

Embodiment 1

A method for connecting a force sensor to a circuit board of an insulin pump, the method comprising:
- a) providing the circuit board, preferably a flexible circuit board, comprising at least one first conductive lead and at least one second conductive lead, wherein the first conductive lead and the second conductive lead are located on the same surface of the circuit board;
- b) providing the force sensor having at least one flexible first contact tab and at least one flexible second contact tab, wherein each contact tab comprises a contact pad, wherein the contact pad of the first contact tab and the contact pad of the second contact tab are arranged on opposite sides relative to each other;
- c) arranging the first contact tab such that the contact pad of the first contact tab faces the first conductive lead of the circuit board;
- d) arranging a first conductive rubber element such that an electrical connection between the contact pad of the first contact tab and the first conductive lead is established;

e) arranging the second contact tab such that the contact pad of the second contact tab and the second conductive lead face in the same direction; and f) arranging a second conductive rubber element such that an electrical connection between the contact pad of the second contact tab and the second conductive lead is established.

Embodiment 2

The method according to the preceding embodiment, wherein the first conductive rubber element is sandwiched in between the first contact tab and the circuit board, wherein a first side of the first conductive rubber element electrically contacts the contact pad of the first contact tab and wherein a second, opposing side of the first conductive rubber element electrically contacts the first conductive lead.

Embodiment 3

The method according to any one of the preceding embodiments, wherein the second conductive rubber element partially overlaps with the second contact tab and with the second conductive lead.

Embodiment 4

The method according to any one of the preceding embodiments, wherein step f) comprises compensating a height difference between the contact pad of the second contact tab and the second conductive lead via the second conductive rubber element.

Embodiment 5

The method according to the preceding embodiment, wherein a first side of the second conductive rubber element electrically contacts the contact pad of the second contact tab and wherein the first side of the second conductive rubber element further electrically contacts the second conductive lead.

Embodiment 6

The method according to any one of the preceding embodiments, wherein a backside of the second contact tab is in physical contact with the circuit board.

Embodiment 7

The method according to the preceding embodiment, wherein the backside of the second contact tab is arranged on a side opposite of the contact pad comprised by the second contact tab.

Embodiment 8

A device for determining a pressure of a fluid in an insulin pump, the device comprising:
- a circuit board, preferably a flexible circuit board, comprising at least one first conductive lead and at least one second conductive lead, wherein the first conductive lead and the second conductive lead are located on the same surface of the circuit board;
- a force sensor having at least one flexible first contact tab and at least one flexible second contact tab, wherein each contact tab comprises a contact pad, wherein the contact pad of the first contact tab and the contact pad of the second contact tab are arranged on opposite sides relative to each other; and
- at least two conductive rubber elements;

wherein the first contact tab is arranged such that the contact pad of the first contact tab faces the first conductive lead of the circuit board, wherein a first conductive rubber element is arranged such that electrical connection between the first contact tab and the first conductive lead is established, wherein the second contact tab is arranged such that the contact pad of the second contact tab and the second conductive lead face in the same direction, wherein a second conductive rubber element is arranged such that an electrical connection between the contact pad of the second contact tab and the second conductive lead is established.

Embodiment 9

The device according to the preceding embodiment, wherein the device further comprises a housing.

Embodiment 10

The device according to the preceding embodiment, wherein the circuit board is fully or partially arranged in the housing.

Embodiment 11

The device according to any one of the two preceding embodiments, wherein the force sensor is fully or partially arranged in the housing.

Embodiment 12

The device according to any one of the three preceding embodiments, wherein the housing comprises at least two cavities, wherein the first cavity is configured for receiving the first conductive rubber element, wherein the second cavity is configured for receiving the second conductive rubber element.

Embodiment 13

The device according to any one of the preceding embodiments referring to a device, wherein the first conductive rubber element is sandwiched in between the first contact tab and the circuit board, wherein a first side of the first conductive rubber element electrically contacts the contact pad of the first contact tab and wherein a second, opposing side of the first conductive rubber element electrically contacts the first conductive lead.

Embodiment 14

The device according to any one of the preceding embodiments referring to a device, wherein the second conductive rubber element partially overlaps with the second contact tab and with the second conductive lead.

Embodiment 15

The device according to any one of the preceding embodiments referring to a device, wherein the second conductive rubber element is configured for compensating a height difference between the contact pad of the second contact tab and the second conductive lead.

Embodiment 16

The device according to any one of the two preceding embodiments, wherein a first side of the second conductive rubber element electrically contacts the contact pad of the second contact tab and wherein the first side of the second conductive rubber element further electrically contacts the second conductive lead.

Embodiment 17

The device according to any one of the preceding embodiments referring to a device, wherein a backside of the second contact tab is in physical contact with the circuit board.

Embodiment 18

The device according to the preceding embodiment, wherein the backside of the second contact tab is arranged on a side opposite of the contact pad comprised by the second contact tab.

Embodiment 19

An insulin pump, comprising:
at least one insulin reservoir;
at least one pump module for delivering insulin to a user; and
at least one device for determining a pressure of a fluid in an insulin pump according to any one of the preceding embodiments referring to a device, wherein the device is arranged for determining an insulin pressure within the insulin pump.

Embodiment 20

The insulin pump according to the preceding embodiment, the insulin pump further comprising a controller operatively connected to the device for determining the pressure of the fluid in the insulin pump, the controller further being configured for detecting an occlusion in the insulin pump by using at least one signal provided by the device for determining the pressure of the fluid in the insulin pump.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
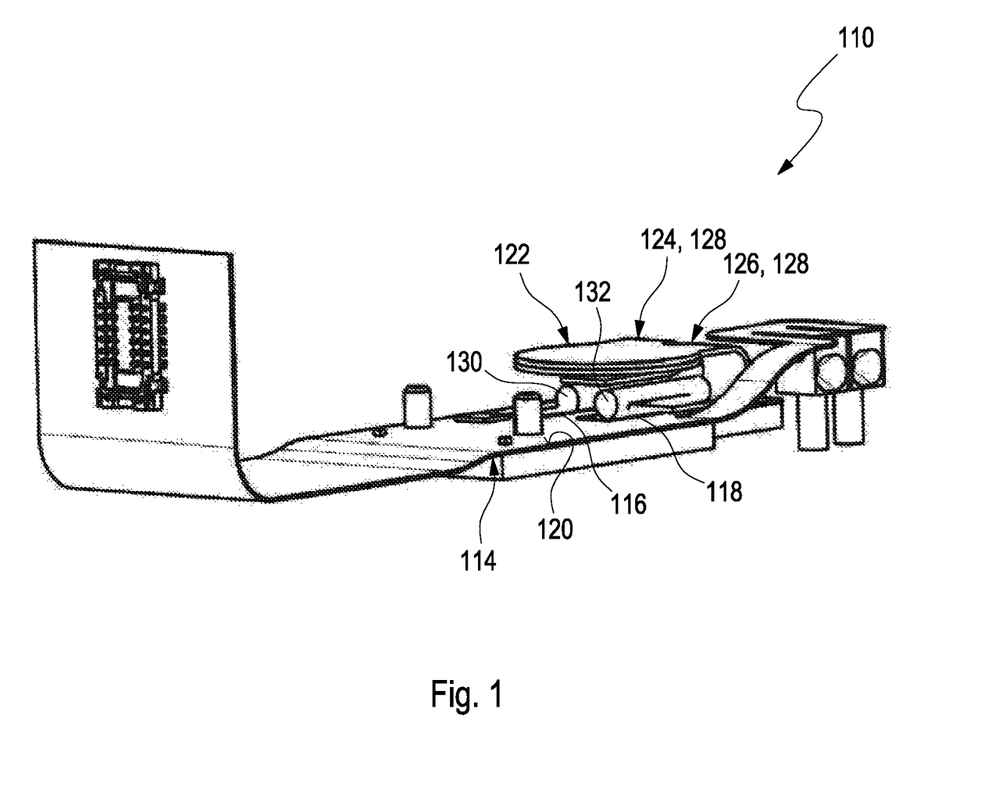
FIG. 1 illustrates an embodiment of a device for determining a pressure of a fluid in an insulin pump in a perspective view.

FIG. 1 illustrates an embodiment of a device 110 for determining a pressure of a fluid in an insulin pump 112 in a perspective view. The device 110 comprises a circuit board 114 comprising at least one first conductive lead 116 and at least one second conductive lead 118. The first conductive lead 116 and the second conductive lead 118 are located in the same surface 120 of the circuit board 114. The device 110 further comprises a force sensor 122 having at least one flexible first contact tab 124 and at least one flexible second contact tab 126. Each contact tab 124, 126 comprises a contact pad 128, wherein the contact pad 128 of the first contact tab 124 and the contact pad 128 of the second contact tab 126 are arranged on opposite sides relative to each other. Further, the device 110 comprises at least a first conductive rubber element 130 and a second conductive rubber element 132.

Figure 2:
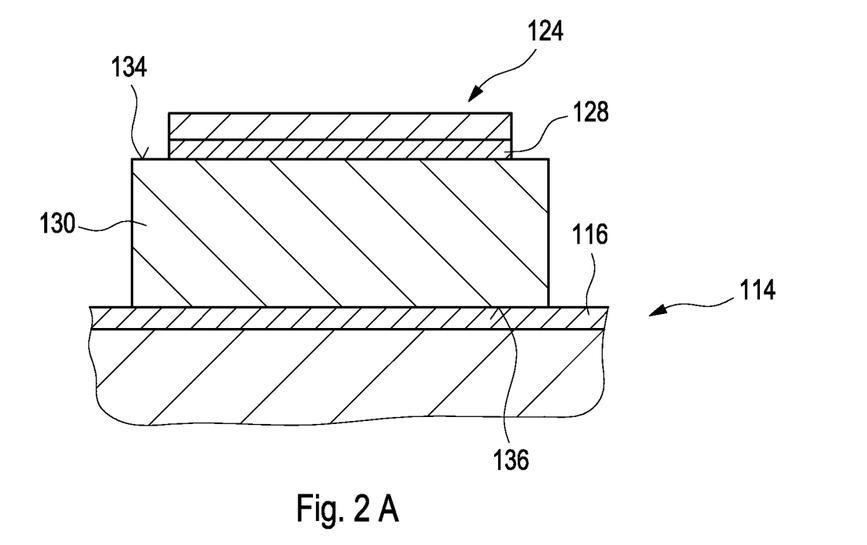
FIGS. 2A and 2B illustrate embodiments of different sections of the device shown in FIG. 1 in sectional views.

In particular, as illustrated in the sectional view in FIG. 2A, the first contact tab 124 is arranged such that the contact pad 128 of the first contact tab 124 faces the first conductive lead 116 of the circuit board 114. Specifically, the first conductive rubber element 130 is arranged such that an electrical connection between the first contact tab 124 and the first conductive lead 116 is established. As further illustrated in FIG. 2A, the first conductive rubber element 130 may specifically be sandwiched in between the first contact tab 124 and the circuit board 114. In particular, a first side 134 of the first conductive rubber element 130 may electrically contact the contact pad 128 of the first contact tab 124 and a second, opposing side 136 of the first conductive rubber element 130 may electrically contact the first conductive lead 116.

As illustrated in the sectional view in FIG. 2B, the second contact tab 126 is arranged such that the contact pad 128 of the second contact tab 126 and the second conductive lead 118 face in the same direction, as shown by arrow 180 in FIG. 2B. Second conductive lead 118 and second contact pad 128 both face and physically contact the second conductive rubber element 132. That is, the second conductive rubber element 132 is arranged such that an electrical connection between the contact pad 128 of the second contact tab 126 and the second conductive lead 118 is established. As further illustrated in FIG. 2B, the second conductive rubber element 132 may partially overlap with the second contact tab 126 and with the second conductive lead 118. In particular, a first side 138 of the second conductive rubber element 132 may for example electrically contact both the contact pad 128 of the second contact tab 126 and the second conductive lead 118. Thereby, the second conductive rubber element 132 may compensate a height difference or gap between the contact pad 128 of the second contact tab 126 and the second conductive lead 118 of the circuit board 114. Specifically, as illustrated in FIG. 2B, the second conductive rubber element may adapt its form to the two elements to be electrically connected, specifically to the contact pad 128 of the second contact tab 126 and to the second conductive lead 118, thereby compensating a height difference between the two elements. Further, a backside 140 of the second contact tab 126 may be in physical contact with the circuit board 114. The backside 140 of the second contact tab may specifically be arranged on a side opposite of the contact pad 128 comprised by the second contact tab 126, as can be seen in FIG. 2B.

Figure 3:
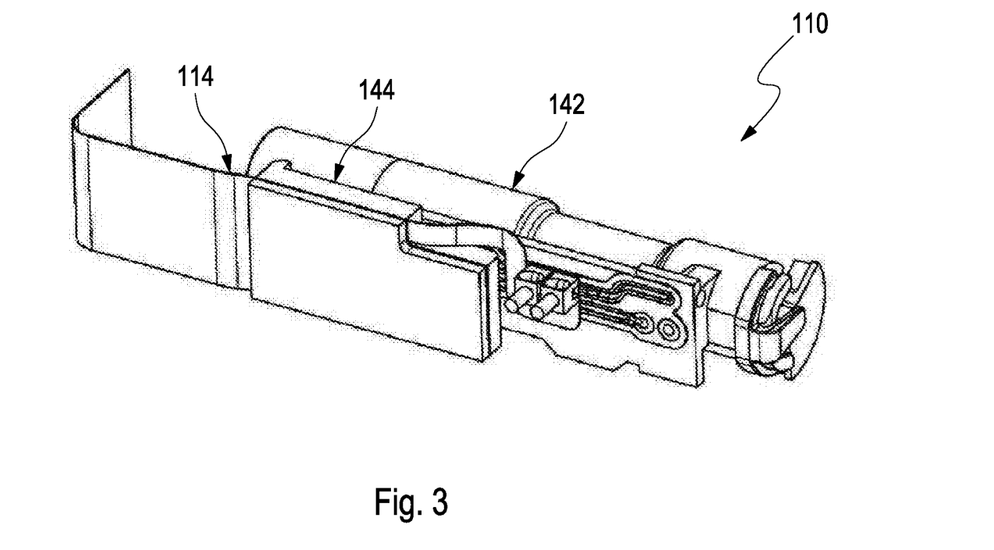
FIG. 3 illustrates an embodiment of a device for determining a pressure of a fluid in an insulin pump in a perspective view.
Figure 4:
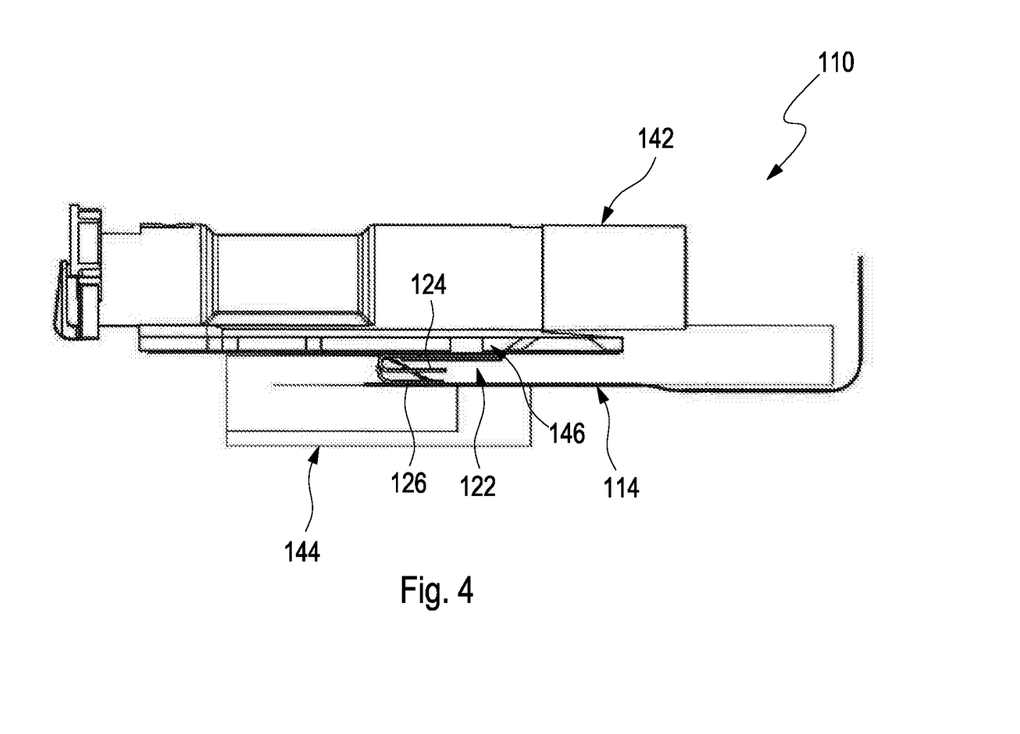
FIG. 4 illustrates an embodiment of a device for determining a pressure of a fluid in an insulin pump in a bottom view.

In FIG. 3 and FIG. 4 embodiments of the device 110 for determining a pressure of a fluid in an insulin pump 112 are illustrated with embodiments of an insulin reservoir 142. As illustrated, the device 110 may for example comprise a housing 144, wherein, specifically, the circuit board 114 may be at least partially arranged in the housing 144. Further, the force sensor 122, specifically the force sensor 122 comprising the first contact tab 124 and the second contact tab 126, may for example be fully arranged in the housing 144. For illustrational purposes, the first conductive rubber element 130 and the second conductive rubber element 132 are not shown in FIG. 4.

Particularly, the force sensor 122 may for example be arranged such that a pressure-sensitive surface or pressure sensitive area of the force sensor 122 may be arranged on an insulin filled conduit extension 146, as illustrated in FIG. 4. Specifically, a fluidic connection may exist between the insulin filled conduit extension 146 and the insulin reservoir 142. In particular, the insulin filled conduit extension 146 may be part of a monitoring system 148 configured for monitoring insulin flow or detecting characteristics, such as for example detecting air bubbles, system pressure or the like. Specifically, the monitoring system 148 may allow a monitoring of the insulin flow, particularly without directly contacting the insulin, e.g., without risk of contaminating the insulin, for example without a physical contact between the insulin and monitoring devices such as for example sensors, e.g., the force sensor 122. In particular, the insulin filled conduit extension 146 may for example be sealed by a flexible element, such as for example a foil, configured for elastically bulging according to a pressure of the fluid, e.g., according to a fluidic pressure of the insulin. As an example, the bulging flexible element may push against the pressure-sensitive surface or area of the force sensor 122, wherein the force sensor 122 may for example be stabilized by the housing 144, such that, as an example, the force sensor 122 may generate an electrical signal according to the fluidic pressure of the insulin.

Figure 5:
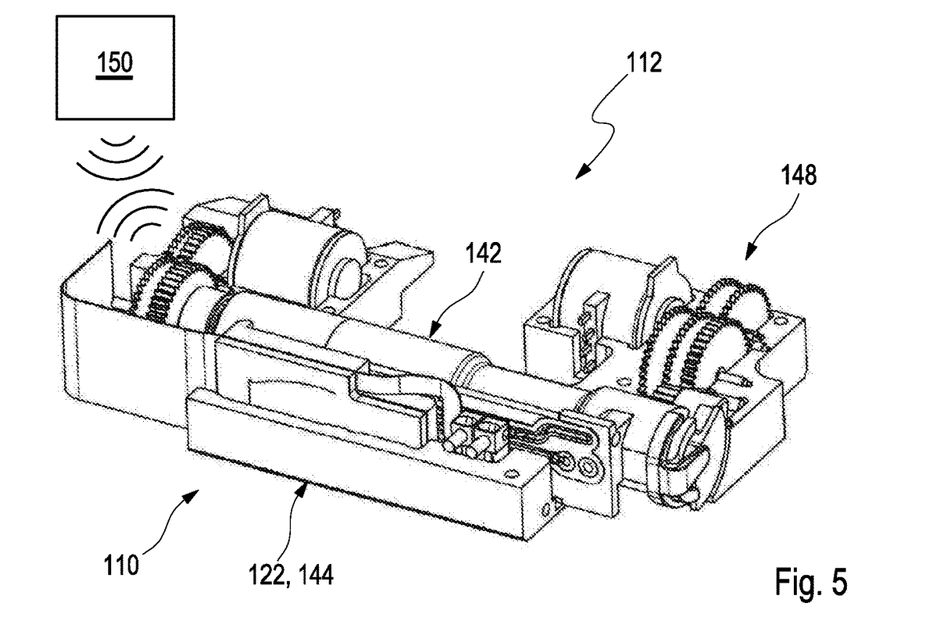
FIG. 5 illustrates an embodiment of an insulin pump.

FIG. 5 illustrates an embodiment of an insulin pump 112 in a perspective view. The insulin pump 112 comprises the insulin reservoir 142 and a pump module 148 for delivering insulin to a user. The insulin pump 112 further comprises the device 110 for determining a pressure of a fluid in the insulin pump 112. Specifically, the device 110 is arranged such as to determine an insulin pressure within the insulin pump 112. In particular, the insulin pump 112 may further comprise a controller 150 operatively connected to the device 110. Specifically, the controller 150 may be connected to the device 110 via a cable or wire, not illustrated in the figure. Alternatively the controller 150 and the device 110 may be connected in a wireless fashion, as illustrated in FIG. 5, such as for example via Bluetooth, near field communication or any other wireless connection. For example, the controller 150 may be configured for detecting an occlusion in the insulin pump 112 by using at least one signal provided by the device 110. The at least one signal may preferably be provided by the force sensor 122 of the device 110, wherein the force sensor 122 may be arranged inside the housing 144.

Figure 6:
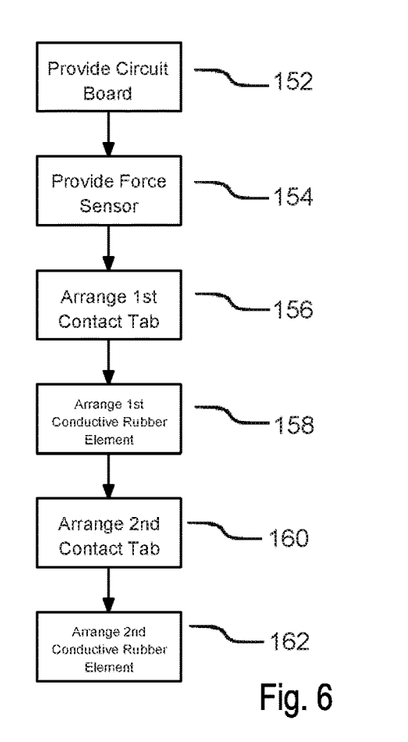
FIG. 6 illustrates an embodiment of a flow chart of a method for connecting a force sensor to a circuit board of an insulin pump.

FIG. 6 illustrates an embodiment of a flow chart of a method for connecting a force sensor 122 to a circuit board 114 of an insulin pump 112. The method comprises step a) (method step 152) of providing the circuit board 114. In particular, the circuit board 114 as exemplarily illustrated in FIG. 1 may be provided, the circuit board 114 comprising at least one first conductive lead 116 and at least one second conductive lead 118, wherein the first conductive lead 116 and the second conductive lead 118 are located on the same surface 120 of the circuit board 114.

Further, the method comprises step b) (method step 154) of providing the force sensor 122. In particular, the force sensor 122 as illustrated in FIG. 1 may be provided, the force sensor 122 comprising a flexible first contact tab 124 and a flexible second contact tab 126. Each contact tab 124, 126 comprises a contact pad 128, the contact pad 128 of the first contact tab 124 and the contact pad 128 of the second contact tab 126 being arranged on opposite sides relative to each other.

The method further comprises step c) (method step 156) of arranging the first contact tab 124 such that the contact pad 128 of the first contact tab 124 faces the first conductive lead 116 of the circuit board 114. Specifically, the contact pad 128 of the first contact tab 124 and the first conductive lead 116 of the circuit board 114 may be arranged such that they are facing each other.

Further, the method comprises step d) (method step 158) of arranging a first conductive rubber element 130 such that an electrical connection between the contact pad 128 of the first contact tab 124 and the first conductive lead 116 is established. In particular, the first conductive rubber element 130 may be sandwiched in between the first contact tab 124 and the circuit board 114, as illustrated in FIG. 2A.

The method further comprises step e) (method step 160) of arranging the second contact tab 126 such that the contact pad 128 of the second contact tab 126 and the second conductive lead 118 face in the same direction. Specifically, a backside 140 of the second contact tab 126 may be in physical contact with the circuit board 114, as illustrated in FIG. 2B. In particular, the backside 140 of the second contact tab 126 may be arranged on a side opposite of the contact pad 128 comprised by the second contact tab 126.

Further, the method comprises step f) (method step 162) of arranging a second conductive rubber element 132 such that an electrical connection between the contact pad 128 of the second contact tab 126 and the second conductive lead 118 is established. Thereby, the second conductive rubber element 132 may compensate a height difference or gap between the contact pad 128 of the second contact tab 126 and the second conductive lead 118, as illustrated in FIG. 2B.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMBERS

| | |
|---|---|
| 110 | device |
| 112 | insulin pump |
| 114 | circuit board |

-continued

LIST OF REFERENCE NUMBERS

| | |
|---|---|
| 116 | first conductive lead |
| 118 | second conductive lead |
| 120 | surface |
| 122 | force sensor |
| 124 | first contact tab |
| 126 | second contact tab |
| 128 | contact pad |
| 130 | first conductive rubber element |
| 132 | second conductive rubber element |
| 134 | first side of first conductive rubber element |
| 136 | second side of first conductive rubber element |
| 138 | first side of second conductive rubber element |
| 140 | backside |
| 142 | insulin reservoir |
| 144 | housing |
| 146 | insulin filled conduit extension |
| 148 | pump module |
| 150 | controller |
| 152 | step a): providing circuit board |
| 154 | step b): providing force sensor |
| 156 | step c): arranging first contact tab |
| 158 | step d): arranging first conductive rubber element |
| 160 | step e): arranging second contact tab |
| 162 | step f): arranging second conductive rubber element |
| 180 | direction faced by contact pad 128 and conductive lead 118 |

What is claimed is:

1. A method for connecting a force sensor to a circuit board of an insulin pump, comprising:
a) providing a circuit board having first and second conductive leads located on the same surface of the circuit board;
b) providing a force sensor with a first flexible contact tab having a first contact pad and a second flexible contact tab having a second contact pad, wherein the first contact pad and the second pad are arranged opposite each other;
c) arranging the first contact pad to face the first conductive lead;
d) arranging a first conductive rubber element to establish an electrical connection between the first contact pad and the first conductive lead, wherein the first conductive rubber element is sandwiched between the first contact tab and the circuit board;
e) arranging the second contact pad and the second conductive lead to face in a same direction; and
f) arranging a second conductive rubber element to establish an electrical connection between the second contact pad and the second conductive lead, wherein a first side of the second conductive rubber element electrically contacts the second contact pad and also electrically contacts the second conductive lead.

2. The method according to claim 1, wherein a first side of the first conductive rubber element electrically contacts the first contact pad and wherein a second, opposing side of the first conductive rubber element electrically contacts the first conductive lead.

3. The method according to claim 1, wherein the second conductive rubber element partially overlaps the second contact tab and the second conductive lead.

4. The method according to claim 1, wherein a backside of the second contact tab physically contacts the circuit board.

5. A device for determining fluid pressure in an insulin pump, the device comprising:
a circuit board having first and second conductive leads located on the same surface of the circuit board;
a force sensor with a first flexible contact tab having a first contact pad and a second flexible contact tab having a second contact pad, wherein the first contact pad and the second pad are arranged opposite each other;
a first conductive rubber element that establishes an electrical connection between the first contact tab and the first conductive lead; and
a second conductive rubber element that establishes an electrical connection between the second contact tab and the second conductive lead, wherein the second contact pad and the second conductive lead face in a same direction;
wherein the first conductive rubber element is sandwiched between the first contact tab and the circuit board and further wherein a first side of the second conductive rubber element electrically contacts the second contact pad and also electrically contacts the second conductive lead.

6. The device according to claim 5, further comprising a housing in which the circuit board and force sensor are fully or partially arranged.

7. The device according to claim 6, wherein the housing comprises a first cavity configured for receiving the first conductive rubber element and a second cavity configured for receiving the second conductive rubber element.

8. The device according to claim 5, wherein a first side of the first conductive rubber element electrically contacts the first contact pad and wherein a second, opposing side of the first conductive rubber element electrically contacts the first conductive lead.

9. The device according to claim 5, wherein the second conductive rubber element partially overlaps the second contact tab and the second conductive lead.

10. The device according to claim 5, wherein the second conductive rubber element compensates for a height difference between the second contact pad and the second conductive lead.

11. The device according to claim 5, wherein a backside of the second contact tab physically contacts the circuit board.

12. An insulin pump, comprising:
an insulin reservoir;
a pump module configured for delivering insulin to a user; and
the device for determining fluid pressure in an insulin pump according to claim 5.

13. The insulin pump according to claim 12, further comprising a controller operatively connected to the device for determining fluid pressure in the insulin pump, the controller configured to detect an occlusion in the insulin pump by using at least one signal provided by the device for determining the pressure of the fluid in the insulin pump.

14. A device for determining fluid pressure in an insulin pump, the device comprising:
a circuit board having first and second conductive leads located on a same surface of the circuit board;
a force sensor with a first flexible contact tab having a first contact pad and a second flexible contact tab having a second contact pad;
a first conductive rubber element sandwiched between the first contact tab and the circuit board, wherein a first side of the first conductive rubber element electrically contacts the first contact pad and a second, opposing side of the first conductive rubber element electrically contacts the first conductive lead, thereby establishing an electrical connection between the first contact tab and the first conductive lead; and a second conductive rubber element that establishes an electrical connection between the second contact tab and the second conductive lead;

wherein a first side of the second conductive rubber element electrically contacts the second contact pad and also electrically contacts the second conductive lead.

15. The device according to claim 14, wherein the first contact tab is arranged on an upper side of the first rubber element relative to the circuit board and the second contact tab is arranged on a lower side of the second rubber element relative to the circuit board.

16. The device of claim 14, wherein the second contact tab is at least partially sandwiched between the second conductive rubber element and the circuit board.

17. The device according to claim 14, further comprising a housing having a first cavity configured for receiving the first conductive rubber element and a second cavity configured for receiving the second conductive rubber element.

18. The device according to claim 14, wherein the second conductive rubber element partially overlaps the second contact tab and the second conductive lead.

* * * * *